US00PP31097P3

(12) United States Plant Patent
Hanna et al.

(10) Patent No.: US PP31,097 P3
(45) Date of Patent: Nov. 19, 2019

(54) GRASS NAMED 'TIFT PA18'

(50) Latin Name: *Pennisetum alopecuroides*
Varietal Denomination: Tift PA18

(71) Applicant: University of Georgia Research Foundation, Inc., Athens, GA (US)

(72) Inventors: Wayne W. Hanna, Chula, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/932,493

(22) Filed: Mar. 6, 2018

(65) Prior Publication Data

US 2019/0281752 P1 Sep. 12, 2019

(51) Int. Cl.
*A01H 5/12* (2018.01)
*A01H 6/46* (2018.01)

(52) U.S. Cl.
USPC ..... Plt./384
CPC ..... *A01H 6/4654* (2018.05)

(58) Field of Classification Search
USPC ..... Plt./384
CPC ..... A01H 5/12; A01H 5/02
See application file for complete search history.

*Primary Examiner* — Kent L Bell
(74) *Attorney, Agent, or Firm* — Klarquist Sparkman, LLP

(57) ABSTRACT

A new variety of *Pennisetum alopecuroides* plant named 'Tift PA18' produces a reduced number of seeds, making it less invasive.

2 Drawing Sheets

Latin name of the genus and species of the plant claimed: 'Tift PA18' is a vegetatively propagated ornamental perennial *Pennisetum* cultivar of the genus and species *Pennisetum alopecuroides*.

Variety denomination: The new *Pennisetum alopecuroides* claimed is of the cultivar denominated 'Tift PA18'.

BACKGROUND OF THE INVENTION

The present invention relates to a new and distinct cultivar of *Pennisetum alopecuroides* herein referred to as 'Tift PA18'.

The new *Pennisetum alopecuroides* is a product of a planned research, evaluation, and testing program conducted by the Inventors in Tifton, Ga. The objective of the *Pennisetum alopecuroides* research program is to create a new plant cultivar with reduced seed production. This cultivar is commercially important for its superior ornamental value and low seed production. These and other qualities are enumerated herein.

Pedigree and history: We evaluated four unpatented morphologically variable accessions maintained at Tifton, Ga. for ornamental potential: 'Tift PS989', 'Tift PS990', 'Tift PS1122', and 'Tift PS1123'. 'Tift PS989' and 'Tift PS1122' were selected as accessions with the most ornamental potential. *Pennisetum alopecuroides* accessions and cultivars are known to produce abundant seed. Seed production in commercial ornamental cultivars of *Pennisetum alopecuroides* tends to make this genus/species invasive, an undesirable trait in landscapes. Seeds from open pollinated 'Tift PS1122' plants were irradiated on 11 Nov. 2010 with 20 Kr of Cobalt 60 gamma radiation. These irradiated seeds were planted to produce a first group of plants. In 2011, this first group of plants were evaluated and eight of these first group of plants were selected. These eight plants were selected as morphologically desirable ornamental genotypes with reduced seed set. Open pollinated seeds were harvested from these eight plants. These seeds from the eight selected plants were re-irradiated on 10 Jan. 2012 with 10 Kr of Cobalt 60 radiation. Only three of the eight plants produced seed that survived this second irradiation. The surviving seed from the three plants were planted to produce 142 plants, numbered consecutively from 1 to 142, that were grown in adjacent rows in a field. These 142 plants were allowed to open pollinate. Irradiation of seeds usually results in chineras or sectors on the plants for the trait of interest. Therefore, each of the 142 plants was divided into four quadrants or sectors (a, b, c, and d) and five or more inflorescences from each quadrant were examined for seed sterility. Sector "a" of plant number 137 (137a) was highly seed sterile and was selected in 2012, and was asexually propagated, to produce 'Tift PA18'. 'Tift PA18' has been tested at Tifton, Ga. and Blairsville, Ga. from 2012 thru 2015. Tests consisted of five and four single plant replications arranged in a randomized complete block experiment at Tifton, Ga. and Blairsville, Ga., respectively. Seven other experimental entries were included in each test. Tift 'Tift PA24' (unpatented) was selected as a seed fertile check with desirable ornamental characteristics from Tift PS1122. Tift 'Tift PA24' also produced abundant pollen for pollinating the experimental seed sterile cultivars in the replicated tests to make sure that the experimental sterile cultivars would not set seed when pollinated with pollen from another genotype.

Asexual reproduction of the new *Pennisetum* 'Tift PA18' by vegetative propagation (single stem propagules) in a controlled environment in Tifton, Ga. in 2012, 2014 and 2015 and in Blairsville, Ga. from 2012 through 2015, has shown that the unique features of this new *Pennisetum* cultivar are stable and reproduced true to type in successive generations.

SUMMARY OF THE INVENTION

The following traits have been repeatedly observed and represent the characteristics of a new *P. alopecuroides* cultivar 'Tift PA18'. The new cultivar 'Tift PA18' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart (5$^{th}$ edition, 2007), published by The Royal Horticultural Society, London, England.

The following traits have been repeatedly observed for the new *P. alopecuroides* cultivar 'Tift PA18' in Tifton, Ga. and Blairsville, Ga. and can be compared to *P. alopecuroides*, 'Tift PA24' (a seed fertile genotype with desirable ornamental characteristics).

1. 'Tift PA18' exhibits a vigorous growth habit.
2. 'Tift PA18' is highly seed sterile.

The new cultivar *Pennisetum* 'Tift PA18' can be compared to *Pennisetum alopecuroides*, 'Tift PA24', a seed fertile and desirable ornamental selection:

Plants of the new *Pennisetum* 'Tift PA18' are compared to 'Tift PA24' in the following characteristics:

1. The new cultivar 'Tift PA18' produces significantly fewer seeds at Tifton, Ga. and Blairsville, Ga. compared to 'Tift PA24'.
2. At Tifton, Ga. the new cultivar 'Tift PA18' produces inflorescences having a height that is typically less than the height of inflorescences of 'Tift PA24'. In addition, leaf heights of 'Tift PA18', except for one year when only slightly shorter, were significantly shorter than 'Tift PA24' at Tifton, Ga.
3. Inflorescence lengths of the new cultivar 'Tift PA18' in most years are similar to those of 'Tift PA24'.
4. The new cultivar 'Tift PA18' produces inflorescence numbers that are greater than the inflorescence numbers of 'Tift PA24'.

The following observations, measurements, and values describe plants grown in Tifton, Ga. and Blairsville, Ga. In Tables 1-7, the least significant difference (LSD) is set at P≤0.05 probability level. Growth days were included in ratings. Plants were spaced 1 meter apart down the row and rows were 2 meters apart. Plants were established as single stem propagules in mid-April to mid-May and rated in September through October. Data were taken from plants during year of establishment at Tifton and Blairsville except 2015 data from Blairsville was taken on plants established in 2014.

'Tift PA18' had inflorescences that were shorter than those of 'Tift PA24' except in 2015 at Blairsville, Ga. Canopy diameter for 'Tift PA18' was less than that of 'Tift PA24' except in 2015 at Blairsville, Ga. This is indicative of the vigor of 'Tift PA18' at the higher elevation of Blairsville, Ga. than Tifton, Ga. The canopy diameter contributes to the beauty of the long arching leaves of these selections before inflorescences are produced. Inflorescence number adds greatly to the beauty of this species. Inflorescence numbers for 'Tift PA18' greater than for 'Tift PA24' (Table 4) in all years. However, inflorescence length for 'Tift PA18' tended to be shorter than 'Tift PA24' in Tifton, Ga. and about the same length as 'Tift PA24' in Blairsville, Ga.

Adaxial leaf color of mature leaves of 'Tift PA18' is Green-143A according to The Royal Horticultural Society color index (5$^{th}$ Edition, 2007), whereas inflorescence color were Greyed Purple 183A for 'Tift PA18'.

Seed set in 'Tift PA18' is significantly reduced.

TABLE 1

Height of inflorescence of two *Pennisetum alopecuroides* grasses ('Tift PA24' is the seed and pollen fertile control) planted at two locations in Georgia.

| | Height of Inflorescence (cm) | | | | | | |
|---|---|---|---|---|---|---|---|
| | Tifton | | | Blairsville | | | |
| Entry | 2012 | 2014 | 2015 | 2012 | 2013 | 2014 | 2015 |
| 'Tift PA18' | 56 | 46 | 52 | 102 | 125 | 101 | 124 |
| 'Tift PA24' | 62 | 51 | 83 | 107 | 126 | 106 | 106 |
| LSD | 6 | 9 | 8 | 9 | 12 | 14 | 9 |
| Growth Days | 180 | 99 | 101 | 178 | 116 | 130 | 155 |

Plant heights were measured from ground level to top of inflorescence. The Tifton tests were planted 18 Apr. 2012, 2 Jun. 2014, and 12 May 2015 and measurements were taken 15 Oct. 2012, 9 Sep. 2014, and 21 Aug. 2015, respectively. The Blairsville tests were planted 14 Apr. 2012, 16 May 2013, and 15 May 2014, and measurements were taken 9 Sep. 2012, 9 Sep. 2013, 22 Sep. 2014 and 24 Sep. 2015 (data taken on 2014 plants), respectively. The least significant difference at the P≤0.05 probability level.

TABLE 2

Height of leaves of two ornamental *Pennisetum alopecuroides* grasses ('Tift PA24' is the seed and pollen fertile control) planted at two locations in Georgia.

| | Height of Leaves (cm) | | | | | | | |
|---|---|---|---|---|---|---|---|---|
| | Tifton | | | | Blairsville | | | |
| Entry | 2012 | 2013 | 2014 | 2015 | 2012 | 2013 | 2014 | 2015 |
| 'Tift PA18' | 72 | 40 | 33 | 37 | 66 | 97 | 47 | 89 |
| 'Tift PA24' | 86 | 41 | 34 | 54 | 60 | 73 | 50 | 83 |
| LSD | 9 | 8 | 7 | 5 | 5 | 9 | 10 | 5 |
| Growth Days | 180 | 170 | 99 | 101 | 148 | 116 | 130 | 155 |

The height of leaves were measured from ground level to top of leaf canopy.

The tests at Tifton were planted 18 Apr. 2012, 13 Apr. 2013, 2 Jun. 2014, and 12 May 2015 and measurements taken 5 Oct. 2012, 30 Sep. 2013, 9 Sep. 2014, and 21 Aug. 2015, respectively. The Blairsville tests were planted 14 Apr. 2012, 16 May 2013, and 15 May 2014, and measurements were taken 9 Sep. 2012, 9 Sep. 2013, 22 Sep. 2014 and 24 Sep. 2015 (data taken on 2014 plants), respectively. The least significant difference at the P≤0.05 probability level.

TABLE 3

Canopy diameter of two ornamental *Pennisetum alopecuroides* grasses ('Tift PA24' is the seed and pollen fertile control) planted at two locations in Georgia.

| | Canopy Diameter (cm) | | | |
|---|---|---|---|---|
| | Tifton | | Blairsville | |
| Entry | 2012 | 2015 | 2014 | 2015 |
| 'Tift PA18' | 77 | 69 | 100 | 159 |
| 'Tift PA24' | 81 | 98 | 123 | 136 |

TABLE 3-continued

Canopy diameter of two ornamental *Pennisetum alopecuroides* grasses ('Tift PA24' is the seed and pollen fertile control) planted at two locations in Georgia.

| | Canopy Diameter (cm) | | | |
|---|---|---|---|---|
| | Tifton | | Blairsville | |
| Entry | 2012 | 2015 | 2014 | 2015 |
| LSD | 10 | 9 | 25 | 7 |
| Growth Days | 180 | 101 | 130 | 155 |

The canopy diameter is the average diameter of the widest and the narrowest diameter of a single plant canopy. The tests at Tifton were planted 18 Apr. 2012 and 12 May 2015 and measurements taken 8 Oct. 2012, and 21 Aug. 2015, respectively. The tests at Blairsville were planted 15 May 2014 and measurements taken 22 Sep. 2014 and 24 Sep. 2015 (data taken on 2014 plants). The least significant difference was set at the P≤0.05 probability level.

TABLE 4

Number of inflorescences per plant of two ornamental *Pennisetum alopecuroides* grasses ('Tift PA24' is the seed and pollen fertile control) planted at two locations in Georgia.

| | Number of Inflorescences | | | | |
|---|---|---|---|---|---|
| | Tifton | | | Blairsville | |
| Entry | 2012 | 2014 | 2015 | 2014 | 2015 |
| 'Tift PA18' | 258 | 156 | 73 | 89 | 120 |
| 'Tift PA24' | 79 | 135 | 62 | 75 | 67 |
| LSD-5% | 33 | 42 | 16 | 43 | 19 |
| Growth Days | 180 | 99 | 101 | 130 | 155 |

Total number of inflorescences were counted per plant. The tests at Tifton were planted 18 Apr. 2012, 13 Apr. 2013, 2 Jun. 2014, and 12 May 2015 and measurements were taken on 15 Oct. 2012, 30 Sep. 2013, 9 Sep. 2014, and 21 Aug. 2015, respectively. The tests at Blairsville were planted 14 Apr. 2012, 16 May 2013, and 15 May 2014, and measurements were taken 9 Sep. 2012, 9 Sep. 2013, 22 Sep. 2014 and 24 Sep. 2015 (data taken on 2014 plants), respectively. The least significant difference was set at the P≤0.05 probability level.

TABLE 5

Inflorescence length of two ornamental *Pennisetum alopecuroides* grasses ('Tift PA24' is the seed and pollen fertile control) planted at two locations in Georgia.

| | Inflorescence Length (cm) | | | | | |
|---|---|---|---|---|---|---|
| | Tifton | | Blairsville | | | |
| Entry | 2012 | 2015 | 2012 | 2013 | 2014 | 2015 |
| 'Tift PA18' | 9 | 8.2 | 14 | 14 | 11 | 15 |
| 'Tift PA24' | 13 | 11.1 | 13 | 15 | 13 | 15 |
| LSD | 1 | 0.8 | 1 | 1 | 2 | 1.4 |
| Growth Days | 180 | 101 | 178 | 116 | 130 | 155 |

Inflorescence length was the mean of three inflorescences per plant. The tests at Tifton were planted 18 Apr. 2012 and 12 May 2015 and measurements taken 15 Oct. 2012 and 21 Aug. 2015, respectively. The tests at Blairsville were planted 14 Apr. 2012, 16 May 2013, and 15 May 2014, and measurements taken 9 Sep. 2012, 9 Sep. 2013, 22 Sep. 2014 and 24 Sep. 2015 (data taken on 2014 plants), respectively. The least significant difference at the P≤0.05 probability level.

TABLE 6

Leaf characteristics of individual plants of two ornamental *Pennisetum alopecuroides* grasses ('Tift PA24' is the seed fertile control) planted at two locations in Georgia.

| | Leaf Length (cm) | | | Leaf Width (mm) | | |
|---|---|---|---|---|---|---|
| | Tifton | | Blairsville | Tifton | | Blairsville |
| Entry | 2012 | 2015 | 2015 | 2012 | 2015 | 2015 |
| 'Tift PA18' | 22.6 | 23.0 | 50 | 6 | 5.5 | 10.2 |
| 'Tift PA24' | 26.8 | 33.6 | 40.2 | 6.5 | 7.4 | 9.6 |
| LSD | 5.1 | 3.3 | 10.9 | 1.4 | 0.7 | 1.1 |

Leaf length (average from three culms) was measured from the leaf collar to the leaf tip of the latest fully extended leaf. Leaf width (average of three culms) was measured in the center of the latest fully extended leaf. The tests at Tifton were planted 18 Apr. 2012 and 12 May 2015 and measurements taken 15 Oct. 2012, and 21 Aug. 2015, respectively. The tests at Blairsville were planted 15 May 2014 and measurements taken 24 Sep. 2015 (data taken on 2014 plants), respectively. The least significant difference was set at the P≤0.05 probability level.

TABLE 7

Seed set per inflorescence and seed germination of six ornamental *Pennisetum alopecuroides* grasses ('Tift PA24' is the seed fertile control) planted at two locations in Georgia.

| | Seeds per Inflorescence | | | | | Seed Germination - % |
|---|---|---|---|---|---|---|
| | Tifton | | Blairsville | | | Blairsville |
| Entry | 2013 | 2015 | 2013 | 2014 | 2015 | 2014 |
| 'Tift PA18' | 0.8 | 0.0 | 6.0 | 0.9 | 0.3 | 22 |
| 'Tift PA24' | 15.4 | 91.5 | 121 | 102 | 71.2 | 93 |
| LSD | 0.3 | 0.0 | 26 | 29.4 | 1.3 | 21 |

Seeds per inflorescence was the mean of four random inflorescences per each replication. Seed germination tests consisted of 25 seeds from four and three different plants (replications) harvested in October 2014 at Tifton and Blairsville, respectively. Germination tests were conducted in April of 2015 to allow seeds to go through a dormancy period and simulate field conditions. The Tifton tests were planted 13 Apr. 2013 and 12 May 2015 and measurements taken in October 2013 and 2015. The Blairsville tests were planted 16 May 2013, and 15 May 2014, and measurements taken 9 Sep. 2013, 22 Sep. 2014 and 24 Sep. 2015 (data taken on 2014 plants), respectively. The least significant differences were set at the P≤0.05 probability level.

TABLE 8

Summary of morphological characteristics of two *Pennisetum alopecuroides* cultivars.

| Trait | Tift 'Tift PA24' | 'Tift PA18' |
|---|---|---|
| Mature inflorescence height | 51-126 cm | 46-125 cm |
| Mature leaf height | 34-86 cm | 33-97 cm |
| Diameter of plant canopy | 81-135 cm | 69-159 cm |
| Inflorescence length | 11.1-15 cm | 9-15 cm |
| Number of Inflorescences per plant | 62-135 | 73-258 |
| Leaf width | 7.4-9.6 mm | 5.5-10.2 mm |
| Leaf length | 26.8-40.2 cm | 22.6-50 cm |
| Adaxial leaf surface trichomes | Glabrous | Glabrous |
| Abaxial leaf surface trichomes | Glabrous | Glabrous |
| Leaf blade margin trichome length | Less than 0.5 mm long | Less than 0.5 mm long |
| Leaf collar trichomes | Dense, 2 mm long | Density, 3 mm long |
| Sheath trichomes | Margins sparse, 1 mm long | Margins moderate, less than 0.5 mm long |
| Ligule | Yes. | Yes |
| Ligule trichomes | Sparse, less than 1 mm long | Less than 1 mm |
| Floret length | 5-6 mm | 5-6 mm |
| Bristle length surrounding florets | 6-19 mm | 8-23 mm |

BRIEF DESCRIPTION OF THE FIGURES

The accompanying colored photographs illustrate the overall appearance and distinct characteristics of the new cultivar of *Pennisetum* 'Tift PA18'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart ($5^{th}$ edition, 2007).

DETAILED DESCRIPTION

Figure 1:
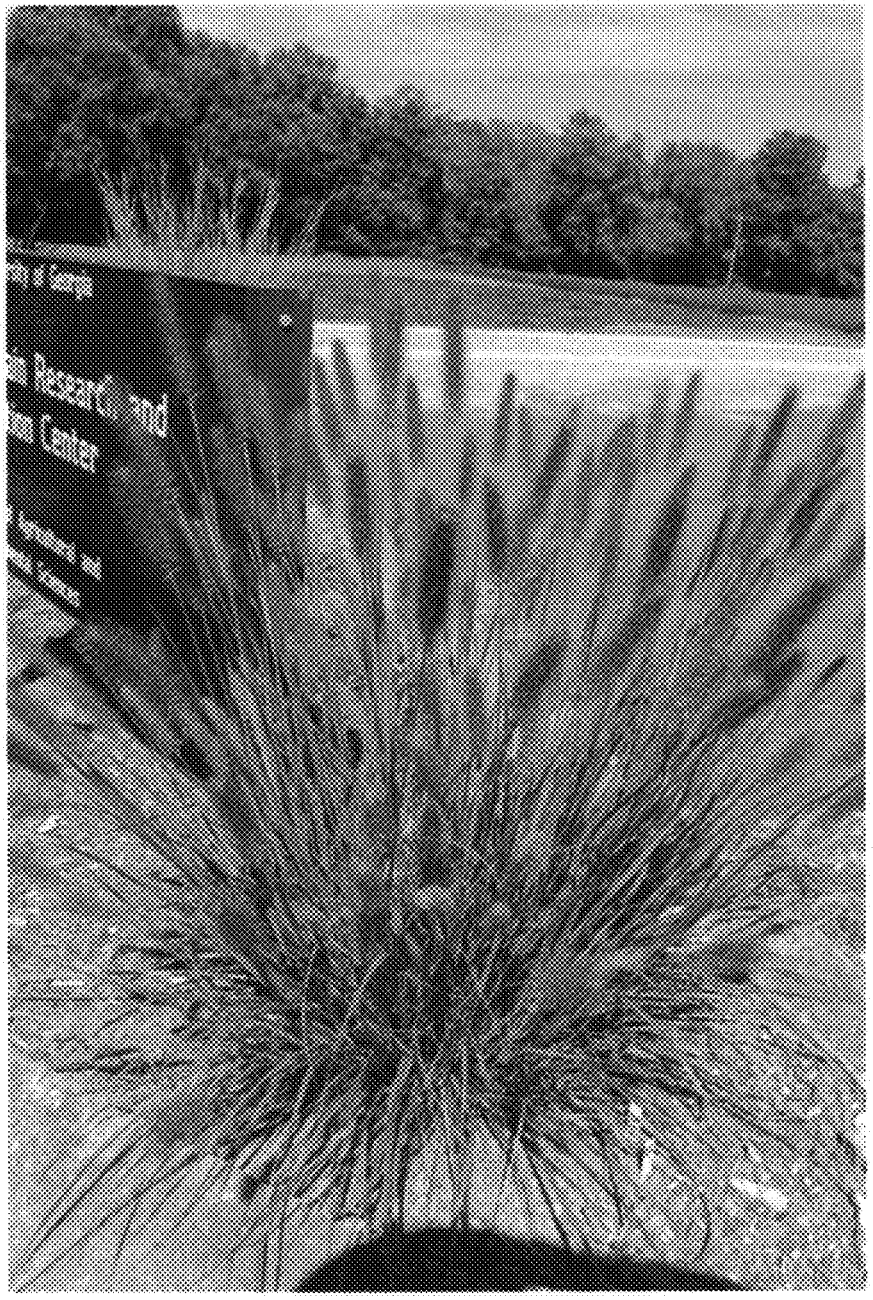
FIG. 1. 'Tift PA18' (year of establishment) in landscape in Union County, Ga.
Figure 2:
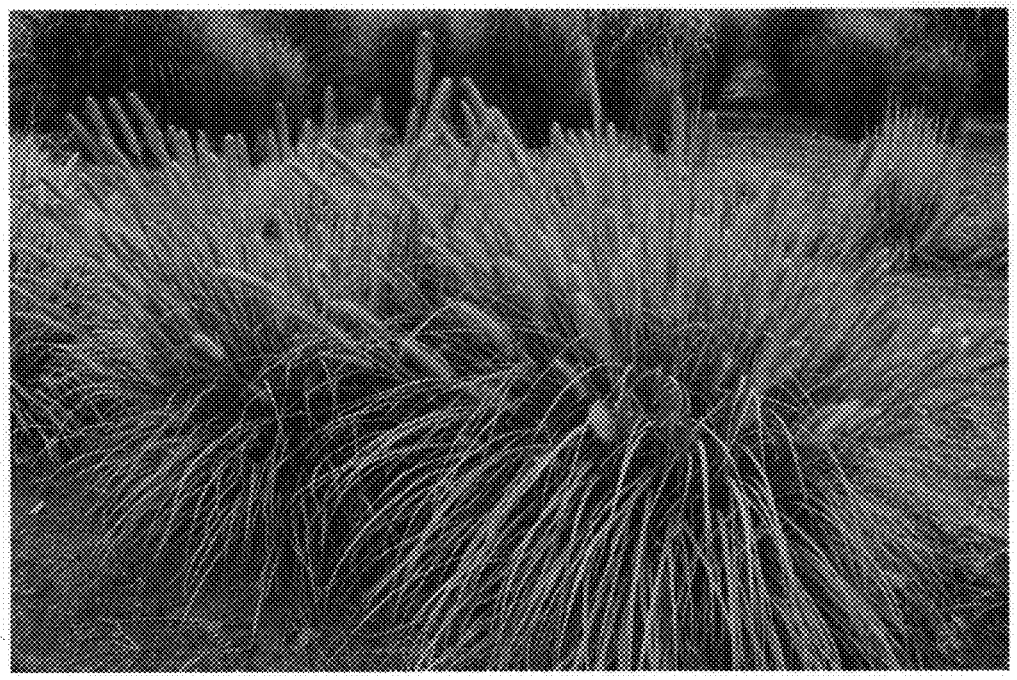
FIG. 2. 'Tift PA18' in research plots (two year old plants) in Union County, Ga.

The new cultivar 'Tift PA18' is a vigorous perennial at Blairsville, Ga. (USDA Zone 7a). The new cultivar 'Tift PA18' survived 90, 95, and 101 days below 0° C. and low temperatures of −9, −29, and −17° C. for the winters of 2012/2013, 2013/2014, and 2014/2015, respectively at Blairsville, Ga.

All data are from plants established as single stem propagules in mid-April to mid-May and rated in September through October, except 2015 data from Blairsville, Ga. was collected from 2014 plants.

Plant:

*Mature inflorescence height.*—46-125 cm.

*Mature leaf height.*—33-97 cm.

*Diameter of plant canopy.*—69-159 cm.

*Inflorescence length.*—9-15 cm.

*Number of inflorescences per plant.*—73-258.

*Number of culms per plant.*—Typically about the same as the number of inflorescences per plant (Table 4) because most of the major culms produce an inflorescence.

Leaf:

*Leaf width.*—5.5-10.2 mm.

*Leaf length.*—22.6-50 cm.

*Adaxial leaf surface trichomes.*—Glabrous.

*Abaxial leaf surface trichomes.*—Glabrous.

*Leaf blade margin trichome length.*—Less than 0.5 mm long.

*Leaf collar trichomes.*—Dense, 3 mm long.

*Sheath trichomes.*—Margin moderate, less than 0.5 mm long.

*Ligule.*—Yes.

*Ligule trichomes.*—Less than 1 mm long.

*Sheath trichomes.*—Moderate, 0.5 mm long.

*Adaxial leaf color.*—Green 143A.

*Abaxial leaf color.*—Green 139C.

*Inflorescence color.*—Greyed Purple 183A.

Although rust (*Puccinia substriata*), leaf spot (*Pyricularia grisea*), and *Helminthosporium* sp. leaf spot are common diseases for *Pennisetum* in Tifton, Ga. due to its humid and warm climate; to date, 'Tift PA18' has not presented any disease symptoms.

No pest susceptibility has been observed for 'Tift PA18'.

Hardiness: 'Tift PA18' has vigorously survived 64, 97 and 96 days below 0° C. and lowest temperatures of −12° C., −18° C. and −17° C., in 2012, 2014, and 1015, respectively in Blairsville, Ga.

What is claimed is:

1. A new and distinct cultivar of *Pennisetum alopecuroides* plant named 'Tift PA18', as illustrated and described herein.

* * * * *